(12) United States Patent
Fry et al.

(10) Patent No.: US 11,556,522 B2
(45) Date of Patent: *Jan. 17, 2023

(54) AUTOMATED DATABASE UPDATING AND CURATION

(71) Applicant: Fry Laboratories LLC, Scottsdale, AZ (US)

(72) Inventors: Stephen Fry, Scottsdale, AZ (US); Jeremy Ellis, Mesa, AZ (US); Matthew Shabilla, Scottsdale, AZ (US)

(73) Assignee: FRY LABORATORIES, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,270

(22) Filed: Apr. 7, 2020

(65) Prior Publication Data
US 2020/0233859 A1 Jul. 23, 2020

Related U.S. Application Data

(63) Continuation of application No. 15/808,630, filed on Nov. 9, 2017, now Pat. No. 10,649,982.

(51) Int. Cl.
*G06F 16/23* (2019.01)
*G06F 16/28* (2019.01)
(Continued)

(52) U.S. Cl.
CPC ...... *G06F 16/2379* (2019.01); *G06F 16/2246* (2019.01); *G06F 16/2474* (2019.01);
(Continued)

(58) Field of Classification Search
None
See application file for complete search history.

(56) References Cited

U.S. PATENT DOCUMENTS

2003/0167283 A1 9/2003 Remsen et al.
2005/0050033 A1* 3/2005 Thomas ................ G16B 50/10
(Continued)

FOREIGN PATENT DOCUMENTS

WO 2005/036369 A2 4/2005

OTHER PUBLICATIONS

Cariisa Shipman, DNA and Its Importance in Taxonomy, Sep. 5, 2015, California Academy of Sciences, retreived from the internet on Jul. 17, 2021, retrieved from URL<https://web.archive.org/web/20150905194557/https://www.calacademy.org/blogs/project-lab/dna-and-its-importance-in-taxonomy> (Year: 2015).*

(Continued)

*Primary Examiner* — Giuseppi Giuliani
(74) *Attorney, Agent, or Firm* — Kilpatrick Townsend & Stockton LLP

(57) ABSTRACT

Systems and methods for retrieval of information from read-only databases that hold taxonomic-related and sequence-related data. A method may include receiving organism names from a taxonomy database and detecting new organism names. The method may also include retrieving hierarchical data and assigning the new organism names to buckets based on the hierarchical data. The method may further include receiving sequence data elements from a nucleotide database, identifying particular buckets to correspond to a screener data set, querying organism names assigned to the particular buckets with names of reference sequences of the sequence data elements, generating a mapping between the sequence data elements and organism names returned as a result of the queries, and storing the mapping.

20 Claims, 6 Drawing Sheets

(51) Int. Cl.
   *G06F 16/22* (2019.01)
   *G06F 16/36* (2019.01)
   *G16B 20/00* (2019.01)
   *G06F 16/2458* (2019.01)
   *G16B 30/10* (2019.01)

(52) U.S. Cl.
   CPC ............ *G06F 16/285* (2019.01); *G06F 16/36* (2019.01); *G16B 20/00* (2019.02); *G16B 30/10* (2019.02)

(56) References Cited

U.S. PATENT DOCUMENTS

| | | |
|---|---|---|
| 2008/0097936 A1* | 4/2008 | Schmidtler ............ G06N 20/10 706/12 |
| 2010/0185577 A1* | 7/2010 | Tsaparas ............... G06F 16/906 706/52 |
| 2010/0198841 A1 | 8/2010 | Parker et al. |
| 2014/0359422 A1 | 12/2014 | Bassett, Jr. et al. |
| 2016/0103958 A1 | 4/2016 | Hebert et al. |
| 2017/0161336 A1 | 6/2017 | Dubey et al. |

OTHER PUBLICATIONS

International Search Report and Written Opinion issued in Application No. PCT/US2018/059609 dated Apr. 8, 2019.

\* cited by examiner

AUTOMATED DATABASE UPDATING AND CURATION

CROSS-REFERENCE TO RELATED APPLICATIONS

This application is a continuation of U.S. application Ser. No. 15/808,630, filed on Nov. 9, 2017, which is hereby incorporated by reference in its entirety for all purposes.

BACKGROUND

The access and management of databases that hold taxonomic-related and sequence-related data has become increasingly complex as the size of these databases has increased exponentially over the last few decades. The retrieval of information from these databases is also complicated by frequent additions, deletions, and modifications of entries, many of which are made at irregular intervals. Apart from the technological difficulties that come with retrieving information from large databases, the representation of taxonomic information raises a number of issues not encountered in other areas. For example, a particular organism may include multiple taxonomic entries (synonyms) which differ in one or more aspects (e.g., spelling) from each other. Thus, a user attempting to retrieve information for a particular organism having knowledge of only one synonym taxonomic entry may be unable to retrieve information held in other synonym taxonomic entries.

Accordingly, there is a need for new methods, systems, and techniques for accessing and managing databases that hold taxonomic-related and sequence-related data.

SUMMARY

In a first aspect of the present disclosure, a method for retrieving information from read-only databases that hold taxonomic-related and sequence-related data is provided. The method may include receiving, from a taxonomy database managed within a first domain, a plurality of organism names. The method may also include detecting, at a computing system, one or more new organism names, of the plurality of organism names, that are not represented in a locally managed database. The method may further include, for each new organism name of the one or more new organism names and at the computing system, retrieving hierarchical data from the taxonomy database, the hierarchical data representing a series of connections that at least partly extend from a representation of the new organism name to one of a set of high-level categories of organism types, each of the set of high-level categories being pre-identified and representing a particular topology level, and assigning the new organism name to a bucket of a set of buckets. In some embodiments, the bucket assignment may be based on a degree of continuity of the series of connections and the one of the set of high-level categories.

In some embodiments, the method may include receiving, at the computing system, a set of sequence data elements from a nucleotide database, the nucleotide database being managed within a second domain, each sequence data element of the set of sequence data elements including a reference sequence and a name of the reference sequence. The method may also include identifying, at the computing system, one or more particular buckets of the set of buckets to correspond to a screener data set. The method may further include for each sequence data element of the set of sequence data elements, querying organism names assigned to the one or more particular buckets with the name of the reference sequence of the sequence data element, generating a mapping between the data corresponding to the sequence data element and an organism name returned as a result of the query, and storing the mapping.

In some embodiments, the method may include receiving a set of reads, each read of the set of reads corresponding to a client, performing an alignment of each read of the set of reads to identify a detected reference sequence, and identifying, based on the mapping, a detected organism name that is mapped to the data corresponding to the detected reference sequence. In some embodiments, the method may include filtering the plurality of organism names to generate a subset of organism names such that each organism name of the subset of organism names is assigned to at least one of the particular set of buckets. In some embodiments, the screener data set comprises the subset of organism names. In some embodiments, the method may include storing the subset of organism names.

In some embodiments, the method may include filtering the set of sequence data elements to generate a subset of sequence data elements such that the data corresponding to each sequence data element of the subset of sequence data elements is mapped to at least one organism name of the subset of organism names. In some embodiments, the method may include storing the subset of sequence data elements. In some embodiments, the method may include sending the subset of organism names, the subset of sequence data elements, and the mapping to an organism detector. In some embodiments, the first domain may be controlled by a first computing system that is separate from the computing system. In some embodiments, the second domain may be controlled by a second computing system that is separate from the computing system and from the first computing system. In some embodiments, identifying the one or more particular buckets of the set of buckets to correspond to the screener data set may include receiving user input indicating the one or more particular buckets.

In some embodiments, the method may include for each new organism name of the one or more new organism names, determining whether the new organism name is characterized as an accepted organism name or a synonym organism name linked to an accepted organism name. In some embodiments, a particular synonym organism name may be linked to a particular accepted organism name when a similarity score associated with the particular synonym organism name and the particular accepted organism name exceeds a predetermined threshold. In a second aspect of the present disclosure, a system is provided. The system may include one or more data processors and a non-transitory computer readable storage medium containing instructions which when executed on the one or more data processors, cause the one or more data processors to perform part or all of one or more methods described herein. In a third aspect of the present disclosure, a computer-program product is provided. The computer-program product may be tangibly embodied in a non-transitory machine-readable storage medium, including instructions configured to cause one or more data processors to perform part or all of one or more methods described herein.

DETAILED DESCRIPTION

Embodiments of the present disclosure relate to database management and retrieval systems. Specifically, embodiments relate to retrieval of information from read-only databases that hold taxonomic-related and sequence-related data. Such data may be updated at irregular intervals and without notice to the computing system retrieving the data. Embodiments of the present disclosure allow efficient retrieval and processing of data from read-only databases by utilizing various data sets and filters that are stored and operated within an automated curator system.

Figure 1:
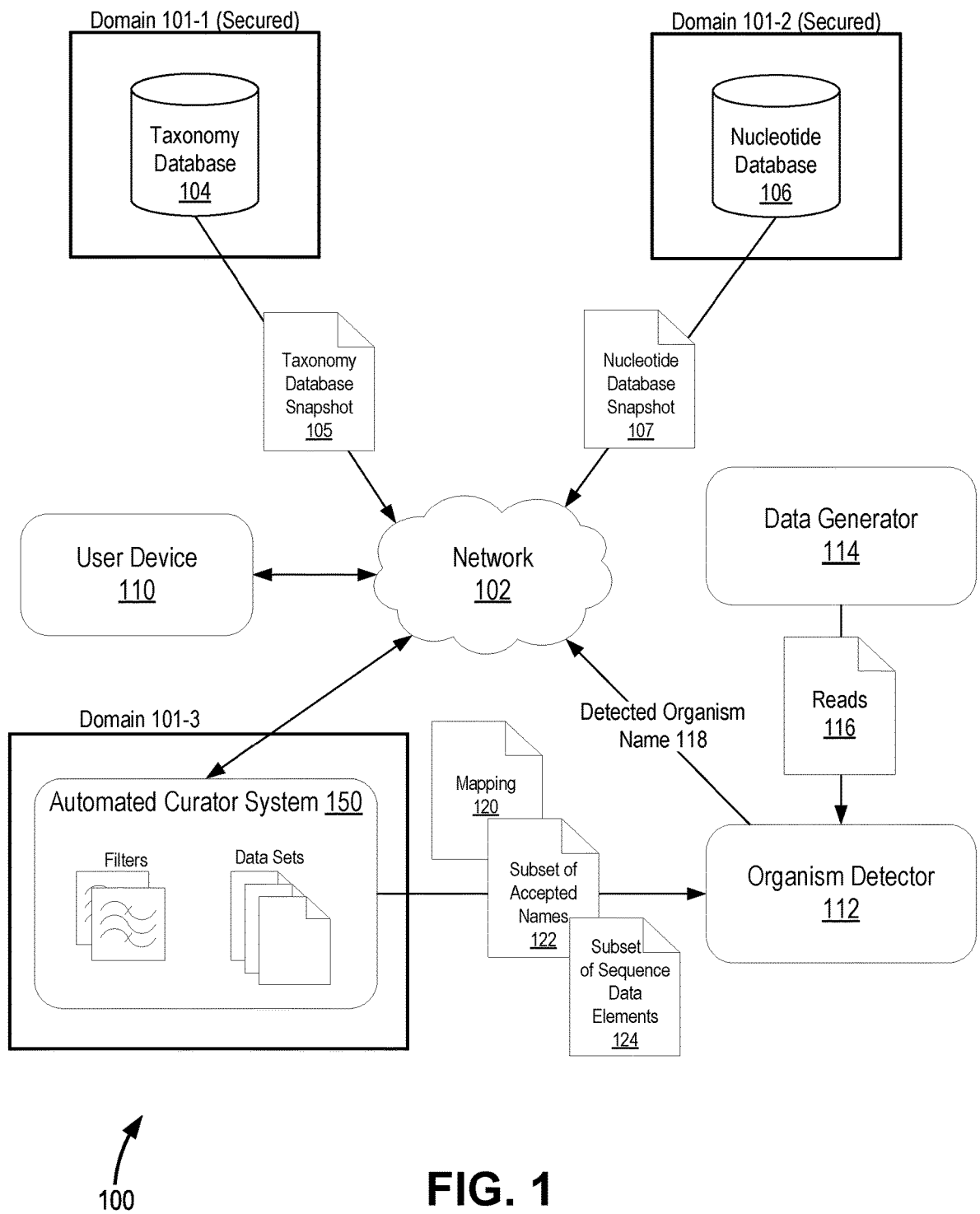
FIG. 1 illustrates a block diagram of a database management and retrieval system, according to an embodiment of the present disclosure.

FIG. 1 illustrates a block diagram of a database management and retrieval system 100, according to an embodiment of the present disclosure. In some embodiments, the various components of database management and retrieval system 100 communicate via a network 102, which may include any one or more of the various available wired and wireless network technologies.

In some embodiments, database management and retrieval system 100 includes a taxonomy database 104 managed within a first secured domain 101-1, a nucleotide database 106 managed within a second secured domain 101-2, and an automated curator system 150 managed within an third domain 101-3. In some embodiments, first secured domain 101-1 is controlled by a first computing system, domain 101-2 is controlled by a second computing system, and third domain 101-3 is controlled by a third computing system. In some embodiments, the first computing system may manage and/or access third domain 101-3 without restriction. However, the first computing system need not manage (e.g., modify) but may have limited access to either of secured domains 101-1 and 101-2. For example, in some embodiments the first computing system may retrieve all or some portion of the data within taxonomy database 104 and nucleotide database 106 in the form of a taxonomy database snapshot 105 and a nucleotide database snapshot 107, respectively. The snapshots may capture everything about the current state of the databases. In some instances, taxonomy database snapshot 105 is retrieved at a specific time such that each entry within taxonomy database snapshot 105 is temporally consistent with every other entry within taxonomy database snapshot 105. Similarly, in some instances nucleotide database snapshot 107 is retrieved at a specific time such that each entry within nucleotide database snapshot 107 is temporally consistent with every other entry within nucleotide database snapshot 107.

In some embodiments, automated curator system 150 may perform several processing operations (described in reference to FIGS. 2-5) on taxonomy database snapshot 105 and nucleotide database snapshot 107. To perform these processing operations, automated curator system 150 may internally maintain various filters and data sets (described in reference to FIGS. 2-5). In some instances, the result of performing these operations is generating various outputs including a mapping 120, a subset of accepted names 122, and a subset of sequence data elements 124, where subset of accepted names 122 is primarily derived from taxonomy database snapshot 105 and subset of sequence data elements 124 is primarily derived from nucleotide database snapshot 107. In some embodiments, mapping 120 is a bidirectional or unidirectional linking between individual accepted names (from subset of accepted names 122) and individual sequence data elements (from subset of sequence data elements 124). Outputs of automated curator system 150 are sent to an organism detector 112.

In some instances, organism detector 112 receives a set of reads 116 from a data generator 114. Each read of set of reads 116 may correspond to a single client and may include a plurality of identifiers (e.g., each identifier identifying a base). After receiving set of reads 116, organism detector 112 may perform an alignment of each read of set of reads 116 to a portion of a reference data set. The reference data set may include an ordered set of identifiers (bases or nucleotides) and/or include a sequence. In some instances, performing the alignment includes both identifying a reference data set (from a set of reference data sets) and then identifying a portion of the data set to which the read aligns. For example, each sequence data element of subset of sequence data elements 124 may include a name and a reference sequence. Organism detector 112 may perform an alignment of each read of set of reads 116 to each of these reference sequences and generate an alignment score for each reference sequence. The score may, but need not, depend on one or more additional factors, such as an empirical likelihood that a corresponding organism has been detected in a population (e.g., a human population). In some instances, the sequence data element having the reference sequence with the highest (or lowest) alignment score is determined to be the detected reference sequence, and the accepted name (of subset of accepted names 122) that is mapped (based on mapping 120) to the detected reference sequence is identified as a detected organism name 118. In some instances, an alignment can be performed using a technique as disclosed in U.S. application Ser. No. 15/630,072, filed on Jun. 22, 2017, which is hereby incorporated by reference in its entirety for all purposes.

In some embodiments, database management and retrieval system 100 includes a data generator 114 for generating reads 116 based on a sample corresponding to a client. In some instances, data generator 114 may process a single sample and generate hundreds of thousands of reads based on the single sample. Data generator 114 may generate reads 116 upon receiving a sample corresponding to a client, or may instead generate reads 116 upon receiving a request from organism detector 112 or from some other component within database management and retrieval system 100 (e.g., user device 110).

In some embodiments, database management and retrieval system 100 includes or communicates with a user device 110, which may submit a request to automated curator system 150 and/or organism detector 112 for detection and/or retrieval of detected organism name 118. The request may specify a particular sample and/or a particular set of reads 116, and may optionally specify a user input 146 in the form of one or more particular buckets $B_1, B_2, \ldots B_N$. Because organism names within taxonomy database snapshot 105 are assigned to one or more buckets, the particular buckets $B_1, B_2, \ldots B_N$ may be used by automated curator system 150 to generate subset of accepted names 122 by querying only the organism names that are assigned to one or more of particular buckets $B_1, B_2, \ldots B_N$.

Figure 2:
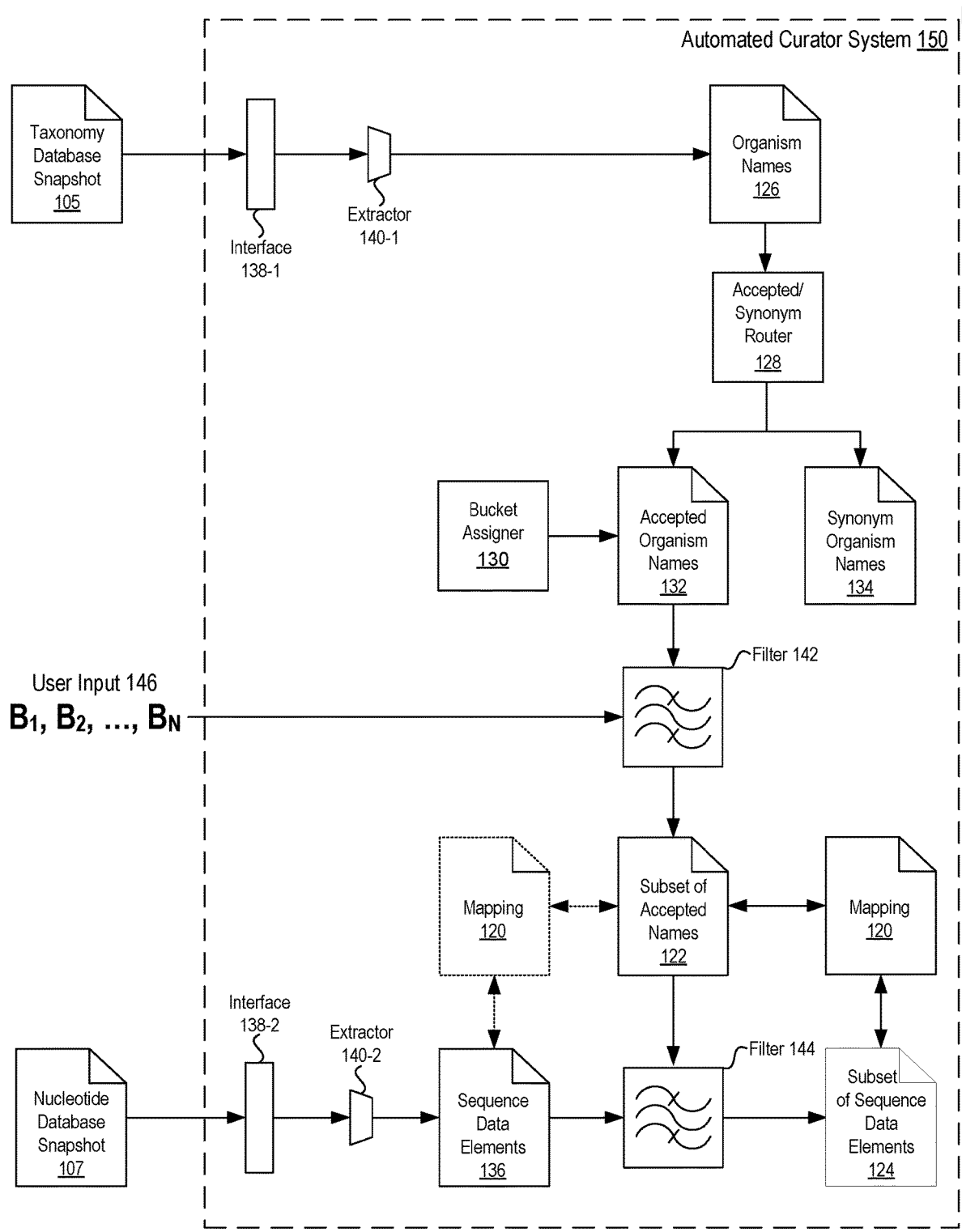
FIG. 2 illustrates a block diagram of an automated curator system, according to an embodiment of the present disclosure.

FIG. 2 illustrates a block diagram of automated curator system 150, according to an embodiment of the present disclosure. Inputs to automated curator system 150 include taxonomy database snapshot 105, nucleotide database snapshot 107, and user input 146, which may be received via one or more interfaces 138 and extractors 140. For example, interface 138-1 may comprise a wireless transceiver configured to receive signals related to taxonomy database snapshot 105 and to digitize the received signals such that extractor 140-1 may extract a plurality of organism names 126. In some embodiments, organism names 126 are characterized as either accepted organism names 132 or as synonym organism names 134 by accepted/synonym router 128. In some embodiments, each organism name is compared to other organism names and a similarity score is generated for each pair. The similarity score may take into account, for example, the number of similar letters in two organism names, the locations of dissimilar letters, the length of the organism names, the number of words in the organism names, among other possibilities. In some embodiments, two organism names are linked to each other when the similarity score associated with the two organism names exceeds a predetermined threshold. In some instances, one of the two organism names is characterized as the accepted organism name and the other is characterized as a synonym organism name linked to the accepted organism name. The accepted name may include a name corresponding to (for example) a particular naming convention and/or standard. In some instances, an accepted name generally is to correspond to a particular naming convention and/or standard but, for each of one or more particular organisms, a different type of accepted name (e.g., one corresponding to a different naming convention and/or standard or one input by a user) is used. The one or more particular organisms can be identified (for example) based on input from a user, distributions of names observed in processed data or another technique.

In some instances, extractor 140-1 may extract metadata for each of the plurality of organism names 126. The metadata may include hierarchical data representing a series of connections that extend from an organism name to high-level categories of organism types. Each of the high-level categories may be pre-identified and may represent a particular topology level. In some embodiments, the similarity score that is generated for a pair of organism names takes into account the metadata for the organism names. For example, two organism names that include a similar series of connections that extend to high-level categories of organism types may have a higher similarity score than two organism names that include dissimilar series of connections.

In some embodiments, after organism names 126 have been characterized and divided into accepted organism names 132 and synonym organism names 134, a bucket assignor 130 may assign each accepted organism name to one or more of a set of buckets. The bucket assignment may be based on a degree of continuity of the series of connections and/or on the particular high-level category of organism types indicated by the hierarchical data for the particular organism name. For example, in some embodiments each organism name with a low degree of continuity of the series of connections are assigned to a particular bucket. As another example, in some embodiments each organism name with a medium and/or high degree of continuity of the series of connections are assigned to a particular bucket. As another example, in some embodiments each organism name having a series of connections that extend to a particular high-level category of organism types are assigned to a particular bucket, and each organism name having a series of connections that extend to a different high-level category of organism types are assigned to a different bucket.

Optionally, in some embodiments, automated curator system 150 may include a filter 142 for filtering accepted organism names 132 to generate subset of accepted names 122. In a first approach, filter 142 is configured to remove all accepted organism names that were not assigned to any of the buckets specified by user input 146. For example, if user input 146 specifies particular buckets $B_1$, $B_3$, and $B_8$, then in some embodiments any accepted organism name that is assigned to any one of buckets $B_1$, $B_3$, and $B_8$ is included in subset of accepted names 122. Alternatively, if user input 146 specifies particular buckets $B_1$, $B_3$, and $B_8$, then in some embodiments any accepted organism name that is only assigned to one or more of buckets $B_1$, $B_3$, and $B_8$ is included in subset of accepted names 122. Other possibilities are contemplated to adjust filter 142 to increase or decrease the size of subset of accepted names 122. In a second approach, filter 142 may be configured to remove all accepted organism names that are not mapped via mapping 120 to any sequence data elements of sequence data elements 136. In some instances, the first approach may be employed as a first filtering step within filter 142 and the second approach may be employed as a second filtering step within filter 142. Using the first and/or the second approach, filter 142 may improve the performance of automated curator system 150 and database management and retrieval system 100 by reducing the size of the utilized list of accepted organism names. For example, in some instances accepted organism names 132 may include a quantity of organism names that is several orders of magnitude larger than subset of accepted names 122.

In some embodiments, interface 138-2 may comprise a wireless transceiver configured to receive signals related to nucleotide database snapshot 107 and to digitize the received signals such that extractor 140-2 may extract a plurality of sequence data elements 136. Each sequence data element of sequence data elements 136 may include a reference sequence and a name of the reference sequence. Each reference sequence may include a plurality of identifiers which are unique for each particular reference sequence. In some embodiments, a filter 144 may filter sequence data elements 136 to generate subset of sequence data elements 124. For example, filter 144 may be configured to remove all sequence data elements that are not mapped via mapping 120 to at least one accepted organism name of subset of accepted names 122. Accordingly, mapping 120 may be generated using subset of accepted names 122 and sequence data elements 136 (indicated by dashed lines in FIG. 2), and after filtering using filter 144, mapping 120 may provide a bidirectional linking of accepted names (from subset of accepted names 122) to sequence data elements (from subset of sequence data elements 124). Filter 144 may improve the performance of automated curator system 150 and database management and retrieval system 100 by reducing the size of the utilized list of sequence data elements. For example, in some instances sequence data elements 136 may include a quantity of sequence data elements that is several orders of magnitude larger than subset of sequence data elements 124.

In some embodiments, filters 142 and 144 are implemented as adaptive filters using digital signal processing techniques. For example, filter 142 may be implemented as an adaptive filter that updates dynamically upon detecting a change in user input 146. This allows user device 110 to modify user input 146 dynamically and immediately observe changes in detected organism name 118. Filter 144 may also be implemented as an adaptive filter that updates dynamically upon detecting a change in user input 146, as changes to filter 142 affect subset of accepted names 122, which in turn affects mapping 120, which in turn affects which sequence data elements of sequence data elements 136 are removed by filter 144.

Figure 3:
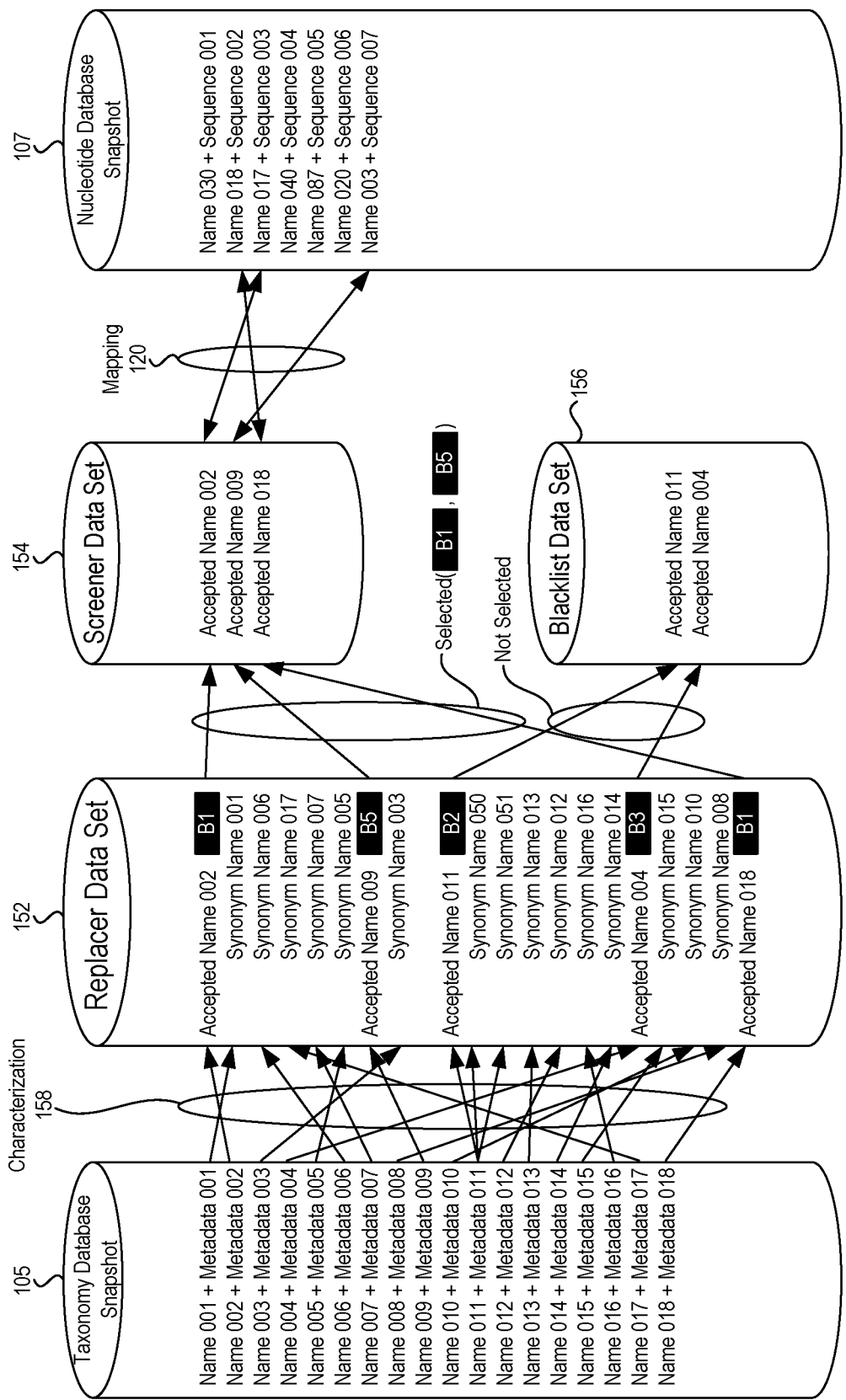
FIG. 3 illustrates various data sets that are maintained within automated curator system, according to an embodiment of the present disclosure.

FIG. 3 illustrates various data sets that are maintained within automated curator system 150, according to an embodiment of the present disclosure. In some instances, automated curator system 150 receives and/or maintains taxonomy database snapshot 105 as described previously, a replacer data set 152, a screener data set 154, a blacklist data set 156, and nucleotide database snapshot 107 as described previously. In some instances, each organism name within taxonomy database snapshot 105 is characterized as either an accepted organism name or as a synonym organism name according to characterization 158 (performed by accepted/synonym router 128). For example, as shown in FIG. 3, Name 001 may be characterized as Synonym Name 001 linked to Accepted Name 002, Name 003 may be characterized as Synonym Name 003 linked to Accepted Name 009, Name 004 may be characterized as Accepted Name 004, etc. Accepted organism names and synonym organism names may be stored within replacer data set 152. In some embodiments, multiple synonym organism names may be generated based on a single organism name. For example, Synonym Name 050 and Synonym Name 051 may be generated based on Name 011, and may consist of alternate spellings of Name 011. Although not shown, in some embodiments nucleotide database snapshot 107 may be placed directly in replacer data set 154.

In some embodiments, each accepted organism name within replacer data set 152 may be assigned to a bucket of a set of buckets. For example, as shown in FIG. 3, Accepted Name 002 may be assigned to Bucket B1, Accepted Name 009 may be assigned to Bucket B5, Accepted Name 011 may be assigned to Bucket B2, Accepted Name 004 may be assigned to Bucket B3, and Accepted Name 018 may be assigned to Bucket B1. In other embodiments, an accepted name may be assigned to multiple buckets (e.g., Buckets B1 and B2) or an accepted name may not be assigned to any buckets. In some instances, a bucket may correspond to a domain-level classification, e.g., bacteria, archaea, eukaryote, virus, etc.

After replacer data set 152 has been updated with accepted and synonym organism names, the accepted organism names are stored in either screener data set 154 or blacklist data set 156 based on the particular buckets specified by user input 146 (as performed by filter 142). In the example shown in FIG. 3, Buckets B1 and B5 are specified by user input 146. Accordingly, Accepted Name 002, Accepted Name 009, and Accepted Name 018 are stored in screener data set 154, and Accepted Name 011 and Accepted Name 004 are stored in blacklist data set 156. In some embodiments, screener data set 154 includes only accepted organism names. In some embodiments screener data set 154 may also include the synonym organism names that are linked to the accepted organism names (e.g., Synonym Name 001, Synonym Name 006, etc.). In some embodiments, blacklist data set 156 includes only accepted organism names. In some embodiments blacklist data set 156 may also include the synonym organism names that are linked to the accepted organism names (e.g., Synonym Name 015, Synonym Name 010, etc.). In some embodiments, replacer data set 152 may maintain organism names as binomials and screener data set 154 may maintain organism names as monomials. In some embodiments, screener data set 154 may instead be used to exclude organism names, e.g., by maintaining a list of the organism names that are neither accepted organism names nor synonym organism names linked to the accepted organism names of screener data set 154 as shown in FIG. 3.

In some embodiments, mapping 120 is generated/updated by linking matching organism names within screener data set 154 and names of sequence data elements within nucleotide database snapshot 107. For example, because Accepted Name 018 within screener data set 154 matches Name 018 within nucleotide database snapshot 107, mapping 120 includes a linking between the two. Mapping 120 may also be generated/updated by linking matching synonym organism names within replacer data set 152 (that are linked to accepted organism names within screener data set 154) and names of sequence data elements within nucleotide database snapshot 107. For example, because Synonym Name 017 within replacer data set 152 (which is linked to Accepted Name 002 within screener data set 154) matches Name 017 within nucleotide database snapshot 107, mapping 120 includes a linking between the two. Therefore, in some embodiments performance of automated curator system 150 may be improved where screener data set 154 additionally includes synonym organism names that are linked to accepted organism names within screener data set 154.

Although FIG. 3 depicts every accepted organism name within screener data set 154 as being mapped to at least one sequence data element within nucleotide database snapshot 107, this may not necessarily be the case in other embodiments. Furthermore, although FIG. 3 depicts not all sequence data elements within nucleotide database snapshot 107 as being mapped to at least one accepted organism name within screener data set 154, this may not necessarily be the case in other embodiments. In reference to FIG. 3, subset of accepted names 122 includes Accepted Name 002, Accepted Name 009, and Accepted Name 018, and subset of sequence data elements 124 includes Name 018+Sequence 001, Name 017+Sequence 003, and Name 003+Sequence 007.

Figure 4:
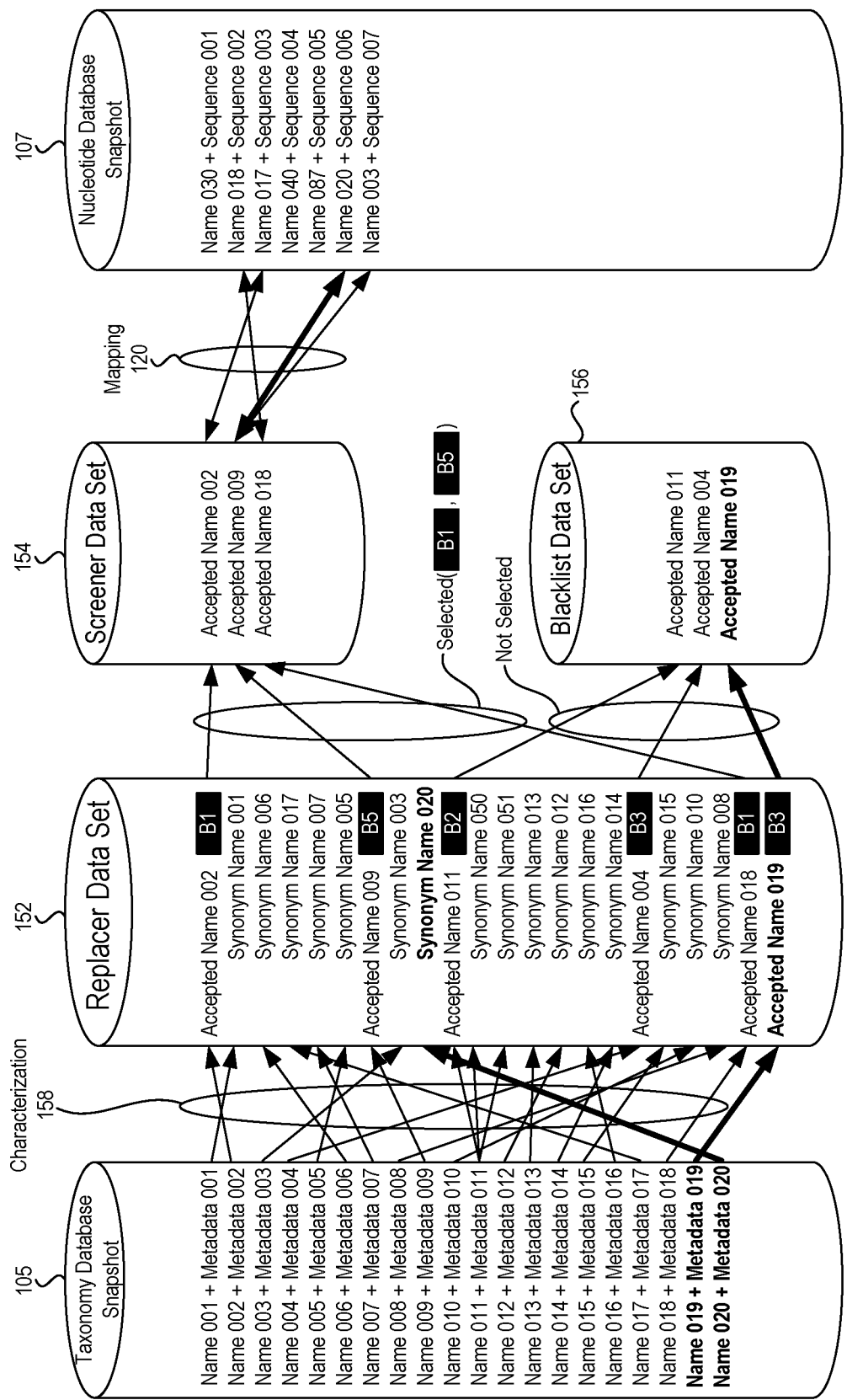
FIG. 4 illustrates various data sets that are maintained within automated curator system, according to an embodiment of the present disclosure.

FIG. 4 illustrates various data sets that are maintained within automated curator system 150, according to an embodiment of the present disclosure. As indicated with bold font and/or arrows with increased thickness, automated curator system 150 may detect new organism names Name 019 and Name 020 which were not included in the previous taxonomy database snapshot 105. In some embodiments, each new organism name may be characterized as either an accepted organism name or as a synonym organism name according to characterization 158 (performed by accepted/synonym router 128), which may result in Name 019 being characterized as an accepted organism name and Name 020 being characterized as a synonym organism name linked to Accepted Name 009. In some embodiments, where an accepted name has no corresponding synonym names, it may be listed in replacer data set 152 without the "Accepted" indication, or it may be removed entirely from replacer data set 152. Accepted Name 019 may then be assigned to Bucket B3. Because Bucket B3 is not included in the particular buckets specified by user input 146, Accepted Name 019 is stored in blacklist data set 156. Because at least one new organism name was detected by automated curator system 150, mapping 120 may be updated by linking Name 020 within nucleotide database snapshot 107 with Accepted Name 009 within screener data set 154 (due to the addition of Synonym Name 020 to replacer data set 152). In reference to FIG. 4, subset of accepted names 122 includes Accepted Name 002, Accepted Name 009, and Accepted Name 018, and subset of sequence data elements 124 includes Name 018+Sequence 001, Name 017+Sequence 003, Name 020+Sequence 006, and Name 003+Sequence 007.

Figure 5:
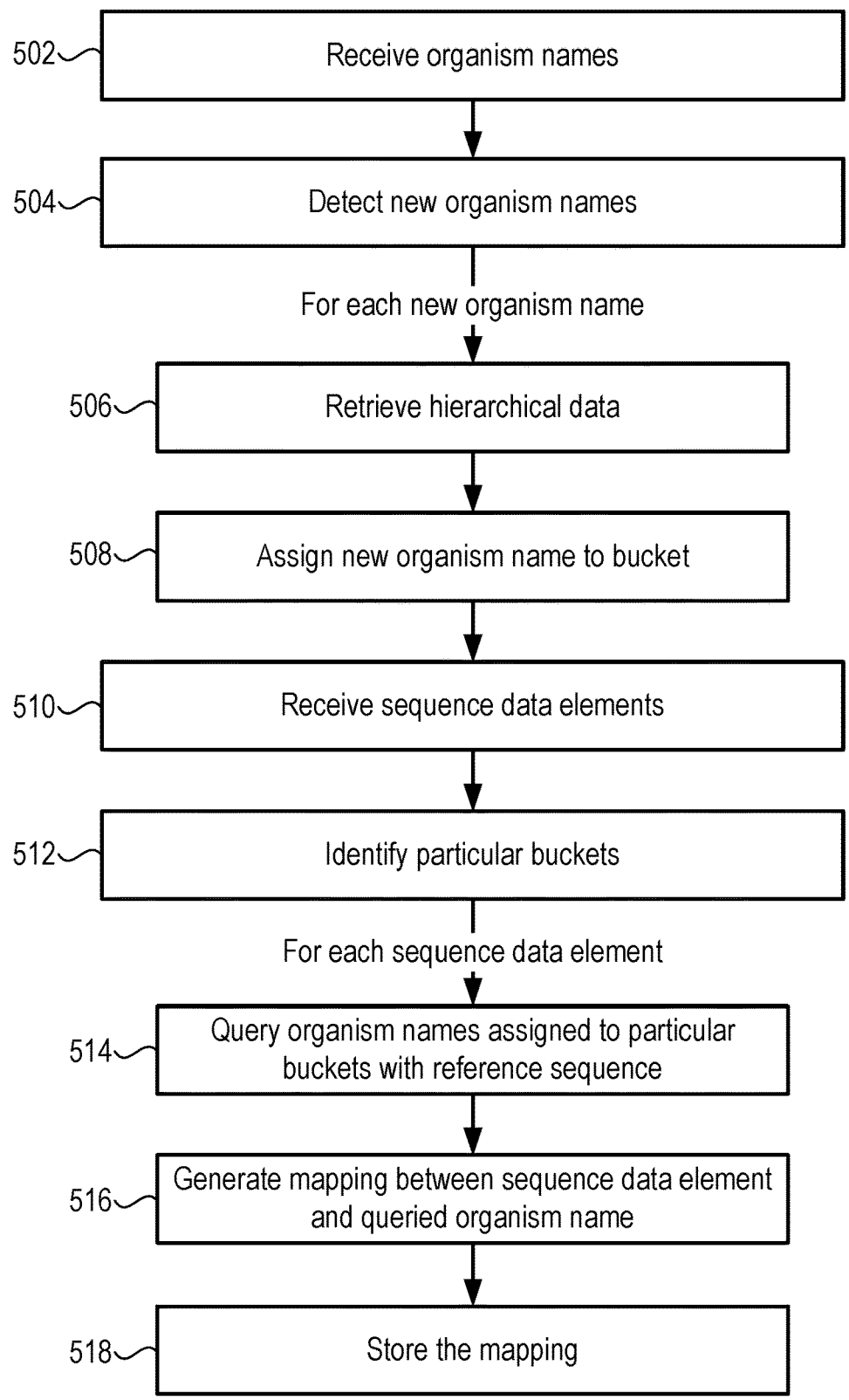
FIG. 5 illustrates a method, according to an embodiment of the present disclosure.

FIG. 5 illustrates a method 500, according to an embodiment of the present disclosure. Operations of method 500 need not be performed in the order shown, and not all operations of method 500 need be performed. For example, in some embodiments operations 502, 508 and/or 518 may be omitted, among other possibilities.

At operation 502, a plurality of organism names are received from a taxonomy database managed within a first domain. One example of the taxonomy database may be the taxonomy database managed by the National Center for Biotechnology Information (NCBI). In some embodiments, the plurality of organism names are received by an automated curator system, such as automated curator system 150. As used in operation 502, the term "receive" may include any action related to retrieving, obtaining, acquiring, getting, gathering, procuring, soliciting, etc. In some embodiments, the first domain is a secured domain such that the automated curator system does not manage (e.g., modify) data within the first domain but may have limited access to data stored therein.

At operation 504, one or more new organism names of the plurality of organism names are detected. In some embodiments, the one or more new organism names are not represented in a locally managed database. For example, the automated curator system may perform a search subroutine for each of the plurality of organism names within all data sets and snapshots stored in the automated curator system. In some instances, the automated curator system may store a list of each organism name previously received so that only a single list need be queried. In some embodiments, operation 504 is followed by an additional operation of, for each new organism name of the one or more new organism names, determining whether the new organism name is characterized as an accepted organism name or as a synonym organism name linked to an accepted organism name. In some embodiments, a particular synonym organism name is linked to a particular accepted organism name when a similarity score associated with the particular synonym organism name and the particular accepted organism name exceeds a predetermined threshold.

Operations 506 and 508 may be performed for each new organism name of the one or more new organism names. At operation 506, hierarchical data is received from the taxonomy database. In some embodiments, the hierarchical data represents a series of connections that at least partly extend from a representation of the new organism name to one of a set of high-level categories of organism types. In some embodiments, each of the set of high-level categories are pre-identified and represent a particular topology level. For example, the set of high-level categories can correspond to a level representing phyla, domain, kingdom, etc. The hierarchical data may be extracted from the metadata associated with each new organism name, and may indicate a single connection or multiple connections that extend from the new organism name to a high-level category of organism type. For example, the hierarchical data for a particular new organism name may include a series of connections that connect nodes corresponding to one or more of: a species, a genus, a family, an order, a class, a phylum, a kingdom, a domain, etc. In one example, the hierarchical data for a particular organism name may include three connections, including a first connection between a particular species and a particular genus, a second connection between the particular genus and a particular class, and a third connection between the particular class and a particular kingdom. In some instances, the set of high-level categories of organism types may include different domains, such as Archaea, Eubacteria, Eukaryota, etc. In some instances, the set of high-level categories of organism types may include different kingdoms, such as Animalia, Plantae, Fungi, Protista, etc. In some instances, the set of high-level categories of organism types may include different phyla, such as Acanthocephala, Annelida, Arthropoda, etc.

It will be appreciated that other types of hierarchical data and/or grouping data are contemplated. For example, the hierarchical data and/or grouping data can include a series of connections that connect nodes corresponding to one or more of Operational Taxonomic Units, Kingdom, Domain, Phylum, Class, Order, Family, Genus, Species, Strain, Variant, Sub-groups, and so on. As another example, the hierarchical data and/or grouping data can include a series of connections that connect nodes corresponding to one or more of Order, Family, Genus and Species.

At operation 508, the new organism name is assigned to a bucket of a set of buckets. In some embodiments, the bucket assignment is based on a degree of continuity of the series of connections and the one of the set of high-level categories. For example, organism names may be assigned to a particular bucket when the degree of continuity of the series of connections is low, and to a different bucket when the degree of continuity of the series of connection is high. The degree of continuity may be low where, for example, a listed genus does not correspond to a listed class, or a listed order does not correspond to a listed kingdom (i.e., listed order is not a member of listed kingdom). In some instances, the degree of continuity may be low where fewer than two or three connections are listed. For example, a particular new organism name having only a listed phylum may be determined to have a low degree of continuity. In some embodiments, organism names are assigned to a particular bucket based on the high-level category to which a particular organism name corresponds. In one example, if the hierarchical data for a particular organism name extends to the high-level category of bacteria, then the particular organism name may be assigned to a first bucket, and if the hierarchical data for a different organism name extends to the high-level category of eukaryote, then the different organism name may be assigned to a second bucket. In some embodiments, operation 508 is followed by an additional operation of filtering the plurality of organism names to generate a subset of organism names such that each organism name of the subset of organism names is assigned to at least one of the particular set of buckets. In some embodiments, the screener data set includes the subset of organism names.

At operation 510, a set of sequence data elements is received from a nucleotide database. In some embodiments, the nucleotide database is managed within a second domain. In some embodiments, each sequence data element of the set of sequence data elements includes a reference sequence and a name of the reference sequence. As used in operation 510, the term "receive" may include any action related to retrieving, obtaining, acquiring, getting, gathering, procuring, soliciting, etc. In some embodiments, the second domain is a secured domain such that the automated curator system may not manage (e.g., modify) data within the second domain but may have limited access to data stored therein.

At operation 512, one or more particular buckets of the set of buckets is identified to correspond to a screener data set. In some embodiments, the one or more particular buckets are specified by a user input generated by a user device. In some embodiments, the screener data set may include all organism names that were assigned to at least one of the one or more particular buckets. In other embodiments, the screener data set may include all organism names that were assigned to each of the one or more particular buckets.

Operations 514, 516, and 518 may be performed for each sequence data element of the set of sequence data elements. At operation 514, organism names assigned to the one or more particular buckets are queried with the name of the reference sequence of the sequence data element. In some embodiments, querying the organism names may include searching for an exact match of the name of the reference sequence. In some embodiments, querying may include searching an exact match or for a synonym name of the name of the reference sequence.

At operation 516, a mapping between the data corresponding to the sequence data element and an organism name returned as a result of the query is generated. Generating the mapping may include forming a bidirectional or unidirectional linking between the sequence data element and the organism name. In some embodiments, generating the mapping may include providing a pointer to the sequence data element in the metadata of the organism name and a pointer to the organism name in the data corresponding to the sequence data element. In some embodiments, operation 516 is followed by an additional operation of filtering the set of sequence data elements to generate a subset of sequence data elements such that the data corresponding to each sequence data element of the subset of sequence data elements is mapped to at least one organism name of the subset of organism names.

At operation 518, the mapping is stored in a local and/or remote data store. In some embodiments, operation 518 is followed by an additional operation of sending the subset of organism names, the subset of sequence data elements, and the mapping to an organism detector. In some embodiments, the organism detector receives the subset of organism names, the subset of sequence data elements, the mapping, and a set of reads, and subsequently performs the operations of performing an alignment of each read of the set of reads to identify a detected reference sequence and identifying, based on the mapping, a detected organism name that is mapped to the data corresponding to the detected reference sequence. The organism detector may send the detected organism name to a user device.

Method 500 provides various advantages for users of read processing systems, particularly systems used to identify an organism name based on a sample. For example, method 500 generates robustness and consistency of database parsing that significantly increases the efficiency of reference sequence and organism name identification. Conventional database management techniques are incapable of either efficient database updating or efficient organism name identification because of various factors, one being the exponential growth and complexity of taxonomic databases over the last few decades. These limitations are overcome in embodiments of the present disclosure due in part to the mapping between the sequence data element and the organism name that is generated at operation 516, which provides a significantly faster means of moving from detected sequence to organism name.

Figure 6:
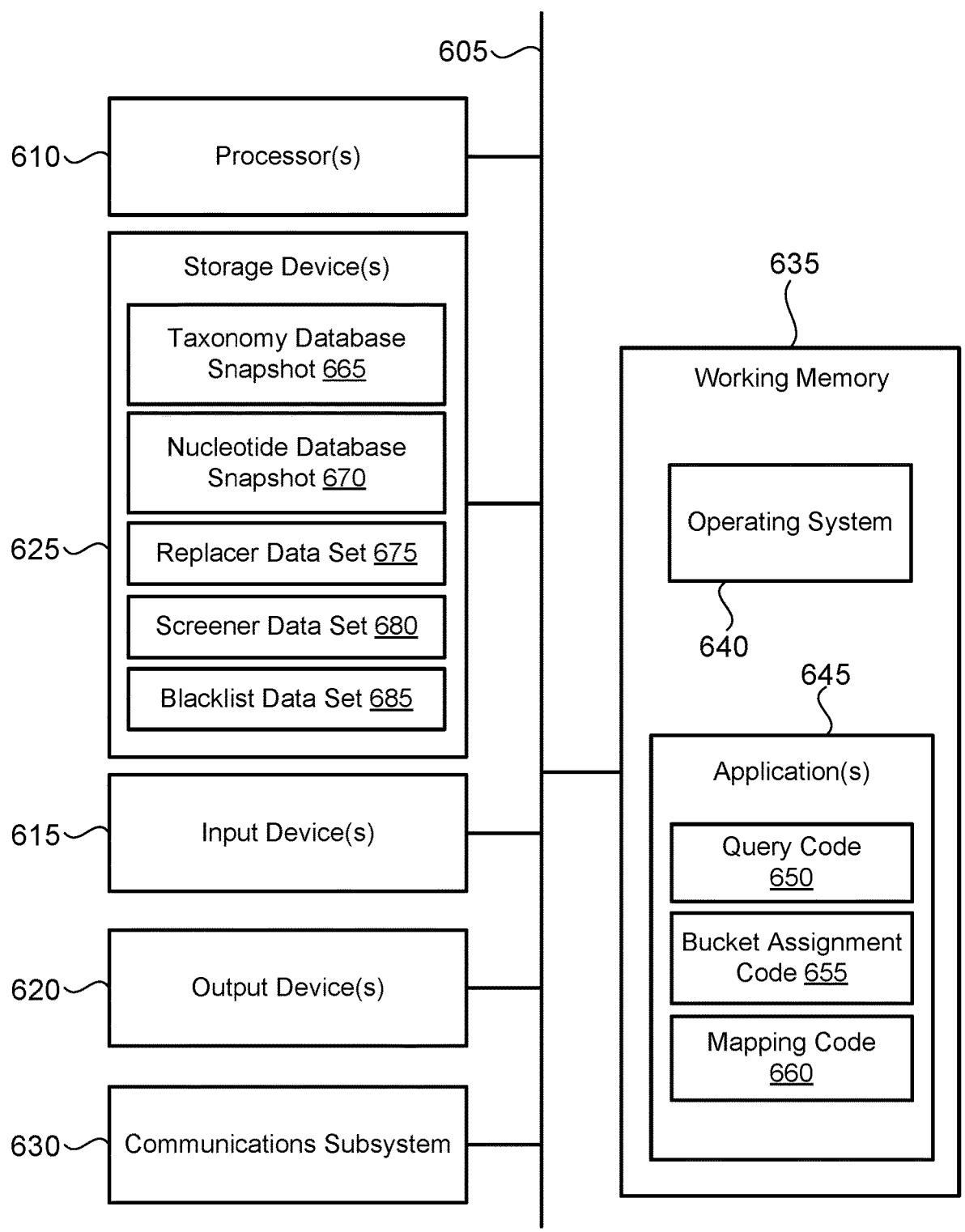
FIG. 6 illustrates a simplified computer system, according to an embodiment of the present disclosure.

FIG. 6 illustrates a simplified computer system 600, according to an embodiment of the present disclosure. A computer system 600 as illustrated in FIG. 6 may be incorporated into devices such as a portable electronic device, mobile phone, or other device as described herein. FIG. 6 provides a schematic illustration of one embodiment of a computer system 600 that can perform some or all of the operations of the methods provided by various embodiments. It should be noted that FIG. 6 is meant only to provide a generalized illustration of various components, any or all of which may be utilized as appropriate. FIG. 6, therefore, broadly illustrates how individual system elements may be implemented in a relatively separated or more integrated manner.

The computer system 600 is shown comprising hardware elements that can be electrically coupled via a bus 605, or may otherwise be in communication, as appropriate. The hardware elements may include one or more processors 610, including without limitation one or more general-purpose processors and/or one or more special-purpose processors such as digital signal processing chips, graphics acceleration processors, and/or the like; one or more input devices 615, which can include, without limitation a mouse, a keyboard, a camera, and/or the like; and one or more output devices 620, which can include, without limitation a display device, a printer, and/or the like.

The computer system 600 may further include and/or be in communication with one or more non-transitory storage devices 625, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The storage device(s) 625 may include a taxonomy database snapshot 665 (which may be similar to taxonomy database snapshot 104), a nucleotide database snapshot 670 (which may be similar to nucleotide database snapshot 106), a replacer data set 675 (which may be similar to replacer data set 152), a screener data set 680 (which may be similar to screener data set 154), and/or a blacklist data set 685 (which may be similar to blacklist data set 156). Other storage devices may be related to mapping 120, subset of accepted names 122, and subset of sequence data elements 124, among other possibilities.

The computer system 600 might also include a communications subsystem 630, which can include, without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 630 may include one or more input and/or output communication interfaces to permit data to be exchanged with a network such as the network described below to name one example, to other computer systems, and/or any other devices described herein. Depending on the desired functionality and/or other implementation concerns, a portable electronic device or similar device may communicate image and/or other information via the communications subsystem 630. In other embodiments, a portable electronic device, e.g. the first electronic device, may be incorporated into the computer system 600, e.g., an electronic device as an input device 615. In some embodiments, the computer system 600 will further comprise a working memory 635, which can include a RAM or ROM device, as described above.

The computer system 600 also can include software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the methods discussed above, might be implemented as code and/or instructions executable by a computer and/or a processor within a computer; in an aspect, then, such code and/or instructions can be used to configure and/or adapt a general purpose computer or other device to perform one or more operations in accordance with the described methods.

In some embodiments, the application programs 645 may include a query code 650 configured to perform a query to determine whether a received organism name has been previously characterized. For example, the query may be configured to determine whether the organism name has previously been assigned to a bucket, mapped to a sequence data element, and/or identified as or associated with a designated accepted organism name. A negative determination of one or more of these assessments may indicate that the organism name is to be further processed. The query code 650 may include code for performing a search function within one or more data stores (e.g., a locally managed database) that attempts to identify a particular organism name.

In some embodiments, the application programs 645 may include a bucket assignment code 655. The bucket assignment code can be configured to assign an organism name (e.g., an organism name associated with a negative query result) with a bucket. The bucket assignment code 655 may include code for analyzing certain aspects of an organism name, as well as code for traversing the series of connections corresponding to the organism name.

In some embodiments, the application programs 645 may include a mapping code 660 configured to generate a mapping between a sequence data element and an organism name. The mapping code 660 may include code for modifying screener data set 680 such that each organism name is associated with a pointer to the mapped sequence data element and for modifying nucleotide database snapshot 670 such that each sequence data element is associated with a pointer to the mapped organism name.

A set of these instructions and/or code may be stored on a non-transitory computer-readable storage medium, such as the storage device(s) 625 described above. In some cases, the storage medium might be incorporated within a computer system, such as computer system 600. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 600 and/or might take the form of source and/or installable code, which, upon compilation and/or installation on the computer system 600 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware or software including portable software, such as applets, etc., or both. Further, connection to other computing devices such as network input/output devices may be employed.

As mentioned above, in one aspect, some embodiments may employ a computer system such as the computer system 600 to perform methods in accordance with various embodiments of the technology. According to a set of embodiments, some or all of the procedures of such methods are performed by the computer system 600 in response to processor 610 executing one or more sequences of one or more instructions, which might be incorporated into the operating system 640 and/or other code, such as an application program 645, contained in the working memory 635. Such instructions may be read into the working memory 635 from another computer-readable medium, such as one or more of the storage device(s) 625. Merely by way of example, execution of the sequences of instructions contained in the working memory 635 might cause the processor(s) 610 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 600, various computer-readable media might be involved in providing instructions/code to processor(s) 610 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 625. Volatile media include, without limitation, dynamic memory, such as the working memory 635.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600.

The communications subsystem 630 and/or components thereof generally will receive signals, and the bus 605 then might carry the signals and/or the data, instructions, etc. carried by the signals to the working memory 635, from which the processor(s) 610 retrieves and executes the instructions. The instructions received by the working memory 635 may optionally be stored on a non-transitory storage device 625 either before or after execution by the processor(s) 610.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional operations not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of operations may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or operations, but they do not preclude the presence or addition of one or more other features, integers, components, operations, acts, or groups.

What is claimed is:

1. A computer-implemented method comprising:
   detecting, at a computing system, that a remote taxonomy database has been updated to include an organism name that is not represented in a particular database, the particular database including organism-name data organized using a set of buckets, wherein each bucket or the set of buckets corresponds to an organism category;
   accessing, by the computing system, metadata corresponding to the organism name, wherein the metadata have been stored at the remote taxonomy database and include two or more taxonomical classifications being associated with the organism name, wherein:
      a first taxonomical classification of the two or more taxonomical classifications identifies a first organism-topology level within an organism taxonomy; and
      a second taxonomical classification of the two or more taxonomical classifications identifies a second organism-topology level within the organism taxonomy, wherein the second organism-topology level is different from the first organism-topology level;
   determining, by the computing system, an extent to which the two or more taxonomical classifications are represented on a same branch within the organism taxonomy, wherein determining the extent to which the two or more taxonomical classifications are represented on the same branch includes determining whether the first organism-topology level and the second organism-topology level correspond to different organism-topology levels of the same branch;
   determining, by the computing system and based on the extent to which the two or more taxonomical classifications are represented on a same branch, that a particular bucket from amongst the set of buckets corresponds to the organism name;
   updating, by the computing system, the particular database to associate the organism name with the particular bucket;
   receiving, at the computing system, biological sequence data; and
   determining, at the computing system, that the biological sequence data corresponds to a reference biological sequence associated with the particular bucket.

2. The computer-implemented method of claim 1, further comprising:
   detecting that a remote nucleotide database has been updated to include a sequence data element that includes a particular biological sequence and a sequence-associated organism name;
   querying one or more of the set of buckets using the sequence-associated organism name;
   detecting a query result indicating that the particular bucket corresponds to the sequence associated organism name; and
   updating the particular database to associate the particular bucket with the particular biological sequence.

3. The computer-implemented method of claim 2, wherein the reference biological sequence for which it is determined that the biological sequence data corresponds includes the particular biological sequence.

4. The computer-implemented method of claim 2, wherein:
   determining that the biological sequence data corresponds to the reference biological sequence includes:
   querying the updated particular database.

5. The computer-implemented method of claim 2, wherein updating the particular database includes generating and storing a mapping between a sequence data element that identifies the particular biological sequence and the particular bucket.

6. The computer-implemented method of claim 1, wherein determining that the biological sequence data corresponds to the reference sequence associated with the particular bucket includes:
   generating, for each bucket of at least some of the set of buckets, an alignment score using the biological sequence data and a bucket-associated reference biological sequence; and
   determining that the biological sequence data corresponds to the reference biological sequence associated with the particular bucket using the alignment scores.

7. The computer-implemented method of claim 1, wherein the biological sequence data is received from a user device in association with a request to identify an organism associated with the biological sequence data.

8. The computer-implemented method of claim 1, wherein the remote taxonomy database is controlled by a first entity and the computing system associated with a different entity.

9. The computer-implemented method of claim 1, wherein the remote taxonomy database and the particular database are controlled by different entities.

10. A system comprising:
   one or more data processors; and
   a non-transitory computer readable storage medium containing instructions which, when executed on the one or more data processors, cause the one or more data processors to perform actions including:
      detecting that a remote taxonomy database has been updated to include an organism name that is not represented in a particular database, the particular database including organism-name data organized using a set of buckets, wherein each bucket or the set of buckets corresponds to an organism category;
      accessing metadata corresponding to the organism name, wherein the metadata have been stored at the remote taxonomy database and include two or more taxonomical classifications being associated with the organism name, wherein:
         a first taxonomical classification of the two or more taxonomical classifications identifies a first organism-topology level within an organism taxonomy; and
         a second taxonomical classification of the two or more taxonomical classifications identifies a second organism-topology level within the organism taxonomy, wherein the second organism-topology level is different from the first organism-topology level;
      determining an extent to which the two or more taxonomical classifications are represented on a same branch within the organism taxonomy, wherein determining the extent to which the two or more taxonomical classifications are represented on the same branch includes determining whether the first organism-topology level and the second organism-topology level correspond to different organism-topology levels of the same branch;
      determining, based on the extent to which the two or more taxonomical classifications are represented on a same branch, that a particular bucket from amongst the set of buckets corresponds to the organism name;
      updating the particular database to associate the organism name with the particular bucket;
      receiving biological sequence data; and
      determining that the biological sequence data corresponds to a reference biological sequence associated with the particular bucket.

11. The system of claim 10, wherein the actions further include:
   detecting that a remote nucleotide database has been updated to include a sequence data element that includes a particular biological sequence and a sequence-associated organism name;
   querying one or more of the set of buckets using the sequence-associated organism name;
   detecting a query result indicating that the particular bucket corresponds to the sequence associated organism name; and
   updating the particular database to associate the particular bucket with the particular biological sequence.

12. The system of claim 11, wherein the reference biological sequence for which it is determined that the biological sequence data corresponds includes the particular biological sequence.

13. The system of claim 11, wherein:
   determining that the biological sequence data corresponds to the reference biological sequence includes:
   querying the updated particular database.

14. The system of claim 11, wherein updating the particular database includes generating and storing a mapping between a sequence data element that identifies the particular biological sequence and the particular bucket.

15. The system of claim 10, wherein determining that the biological sequence data corresponds to the reference sequence associated with the particular bucket includes:
   generating, for each bucket of at least some of the set of buckets, an alignment score using the biological sequence data and a bucket-associated reference biological sequence; and
   determining that the biological sequence data corresponds to the reference biological sequence associated with the particular bucket using the alignment scores.

16. The system of claim 10, wherein the biological sequence data is received from a user device in association with a request to identify an organism associated with the biological sequence data.

17. A computer-program product tangibly embodied in a non-transitory machine-readable storage medium, including instructions configured to cause one or more data processors to perform actions including:
   detecting that a remote taxonomy database has been updated to include an organism name that is not represented in a particular database, the particular database including organism-name data organized using a set of buckets, wherein each bucket or the set of buckets corresponds to an organism category;
   accessing metadata corresponding to the organism name, wherein the metadata have been stored at the remote taxonomy database and include two or more taxonomical classifications being associated with the organism name, wherein:
      a first taxonomical classification of the two or more taxonomical classifications identifies a first organism-topology level within an organism taxonomy; and
      a second taxonomical classification of the two or more taxonomical classifications identifies a second organism-topology level within the organism taxonomy, wherein the second organism-topology level is different from the first organism-topology level;

determining an extent to which the two or more taxonomical classifications are represented on a same branch within the organism taxonomy, wherein determining the extent to which the two or more taxonomical classifications are represented on the same branch includes determining whether the first organism-topology level and the second organism-topology level correspond to different organism-topology levels of the same branch;

determining, based on the extent to which the two or more taxonomical classifications are represented on a same branch, that a particular bucket from amongst the set of buckets corresponds to the organism name;

updating the particular database to associate the organism name with the particular bucket;

receiving biological sequence data; and determining that the biological sequence data corresponds to a reference biological sequence associated with the particular bucket.

18. The computer-program product of claim 17, wherein the actions further include:

detecting that a remote nucleotide database has been updated to include a sequence data element that includes a particular biological sequence and a sequence-associated organism name;

querying one or more of the set of buckets using the sequence-associated organism name;

detecting a query result indicating that the particular bucket corresponds to the sequence associated organism name; and updating the particular database to associate the particular bucket with the particular biological sequence.

19. The computer-program product of claim 18, wherein the reference biological sequence for which it is determined that the biological sequence data corresponds includes the particular biological sequence.

20. The computer-program product of claim 18, wherein:

determining that the biological sequence data corresponds to the reference biological sequence includes:

querying the updated particular database.

* * * * *